United States Patent [19]

Courty et al.

[11] Patent Number: 4,780,481

[45] Date of Patent: Oct. 25, 1988

[54] PROCESS FOR MANUFACTURING A MIXTURE OF PRIMARY ALCOHOLS FROM A SYNTHESIS GAS, IN THE PRESENCE OF A CATALYST CONTAINING COPPER, COBALT, ZINC AND AT LEAST ONE ALKALI AND/OR ALKALINE EARTH METAL

[75] Inventors: Philippe Courty, Houilles; Patrick Chaumette, Bougival; Daniel Durand; Catherine Verdon, both of Rueil-Malmaison, all of France

[73] Assignee: Institut Francais du Petrole, Rueil-Malmaison, France

[21] Appl. No.: 26,493

[22] Filed: Mar. 16, 1987

[30] Foreign Application Priority Data

Mar. 17, 1986 [FR] France ............................. 86 03875

[51] Int. Cl.$^4$ ............................................. C07C 27/06
[52] U.S. Cl. ..................................... 518/713; 518/700; 502/302
[58] Field of Search ............................. 518/700, 713

[56] References Cited

U.S. PATENT DOCUMENTS

| | | |
|---|---|---|
| 4,122,110 | 10/1978 | Sugier et al. . |
| 4,291,126 | 9/1981 | Sugier et al. . |
| 4,346,179 | 8/1982 | Sugier et al. . |
| 4,440,668 | 4/1984 | Chang et al. . |
| 4,552,861 | 11/1985 | Courty et al. . |
| 4,559,316 | 12/1985 | Mazanec et al. ................ 518/713 |
| 4,576,968 | 3/1986 | Nay et al. ........................ 518/713 |
| 4,596,782 | 6/1986 | Courty et al. . |
| 4,659,742 | 4/1987 | Courty et al. . |

FOREIGN PATENT DOCUMENTS 0110357  6/1984  European Pat. Off. .

Primary Examiner—Howard T. Mars
Attorney, Agent, or Firm—Millen & White

[57] ABSTRACT

A process for manufacturing a mixture of saturated primary alcohols by reacting carbon oxides with hydrogen in the presence of a catalyst formed essentially of the following elements: copper, cobalt, zinc, at least one metal A selected from the group consisting of alkali and alkaline earth metals and optionally zirconium and/or at least one metal M selected from the group formed of scandium, yttrium and rare earth metals and/or at least one metal N selected from group VIII noble metals, the proportion by weight of each metal element being: copper: 15–55%, colbalt: 5–25%, zinc: 15–70%, metal A: 0.01–5%, zinconium: 0–55%, metal M: 0–20%, metal N: 0–1%, the total amount by weight of zinc and zirconium in percent by weight of all the metals being from 15 to 70% and the atomic ratios between these metals being: Cu/Co: 0.2:1 to 5:1 and Zn/(Zn+Zr): 0.05:1 to 1:1 and (Zn+Zr)/Co: 0.5:1 to 8:1.

The catalyst may be prepared by complexing or by coprecipitating catalytic elements.

18 Claims, No Drawings

PROCESS FOR MANUFACTURING A MIXTURE OF PRIMARY ALCOHOLS FROM A SYNTHESIS GAS, IN THE PRESENCE OF A CATALYST CONTAINING COPPER, COBALT, ZINC AND AT LEAST ONE ALKALI AND/OR ALKALINE EARTH METAL

The present invention relates to a catalytic process for manufacturing a mixture of methanol and higher alcohols by reacting carbon oxides with hydrogen. The obtained alcohols are mainly saturated primary alcohols. The process according to the invention gives saturated linear primary alcohols of 2 or more carbon atoms with a good selectivity.

BACKGROUND OF THE INVENTION

U.S. Pat. Nos. 4,122,110 and 4,291,126 and the French patent application Nos. 2,523,957 and 2,564,091, corresponding to U.S. patent application Ser. No. 478,764 filed on Mar. 25, 1983 and Ser. No. 732,488 filed on May 10, 1985, have disclosed catalysts used in a process for manufacturing an alcohol mixture from CO, $H_2$ or CO, $CO_2$, $H_2$ mixtures. These catalysts generally have a good selectivity in the conversion of carbon oxides and hydrogen to alcohols and their selectivity to saturated linear primary alcohols of 2 or more carbon atoms is often higher than 70% by weight. Finally they have a high initial productivity, mostly higher than or equal to about 0.1 ton on alcohols per ton of catalyst and per hour.

These catalysts usually comprise at least three essential elements: copper, cobalt and at least one alkali and/or alkaline earth metal.

The catalysts disclosed in U.S. Pat. No. 4,122,110 further contain at least one metal M selected from the group formed of chromium, iron, vanadium and manganese and optionally zinc, and/or magnesia and/or an aluminous cement.

The catalysts disclosed in U.S. Pat. No. 4,291,126 contain, in addition to the elements mentioned for the catalysts disclosed in U.S. Pat. No. 4,122,110, at least one metal from the group of rare earths having atomic numbers from 57 to 71 inclusive, and optionally at least one additional noble metal from group VIII of the periodic classification of elements (Handbook of Chemistry and Physics 37$^{th}$ edition 1955–1956 p. 392–393).

The catalysts disclosed in the French patent application No. 2,523,957 contain, in addition to the above-mentioned essential elements, alumina and optionally zinc, at least one metal M selected from the group formed of manganese, vanadium, iron and rhenium, at least one metal N selected from the group formed of scandium, yttrium, thorium, zirconium and rare earth metals of atomic numbers from 57 to 71 inclusive, chromium and at least one noble metal from group VIII of the periodic classification of elements.

The catalysts disclosed in the above-mentioned documents contain the mentioned metal elements in well defined weight proportions and atomic ratios.

The European patent application No. 110,357 discloses catalysts containing at least four elements in their formula, such for example as:

Copper, nickel, at least one alkali and/or alkaline-earth metal and at least one metal from groups $II_A$, $III_A$, $IV_A$, $II_B$, $III_B$, $IV_B$ and the fourth period of groups $V_B$, $VI_B$, and $VII_B$ of the periodic classification of elements; or zinc, at least one compound selected from the group formed of iron, cobalt and nickel, at least one alkali and/or alkaline earth metal and at least one metal from groups $II_A$, $III_A$, $IV_A$, $II_B$, $III_B$, $IV_B$ and the fourth period of groups $V_B$, $VI_B$, $VII_B$ of periodic classification of elements.

U.S. Pat. No. 4,440,668 discloses catalysts containing essentially three compounds deriving from the following metals:
1. Copper,
2. a metal selected from the metals of groups $VI_B$, $VII_B$ and the non noble metals of group VIII,
3. a metal selected from groups $IV_B$ and $V_B$.

These catalysts also preferably contain 1 to 20% by weight of at least one alkali metal.

The European patent application No. 100,607 discloses catalysts containing at least four essential elements:
1. cobalt,
2. at least one metal selected from the group consisting of copper, silver, gallium, zirconium, zinc and thorium,
3. at least one metal selected from the group consisting of palladium, platinum and nickel, and
4. at least one alkali metal.

The alcohols obtained by the processes conducted in the presence of the above-mentioned catalysts have many applications. The high proportion of $C_2$–$C_6$ alcohols thus obtained make advantageous the use of them in admixture with hydrocarbon cuts to form mixed hydrocarbon-alcohol motor-fuels.

As a matter of fact, the higher alcohols are more compatible with hydrocarbons than methanol; they also facilitate the incorporation of said methanol with hydrocarbons.

However, the processes for alcohol synthesis using the above-mentioned catalytic compositions generally suffer from various disadvantages:

Relatively high amounts of hydrocarbons are produced together with the alcohols.

When contacted with the synthesis gas, the above-mentioned catalysts may generate a transitory methanation reaction, highly exothermic, which requires the progressive substitution of the synthesis gas for the inert gas introduced in the unit before admission of the synthesis gas (after reduction with hydrogen and before admission of the synthesis gas).

In the presence of the above-mentioned metal elements, the thermal stabilization of the copper-cobalt pair generally requires the addition of a high proportion of alkali metals, generally resulting in a reduced purity of the produced alcohol mixture.

For all these reasons, the procedures of conditioning the catalyst under hydrogen and/or reactive gases are generally complex, (French patent 2 593 957 and French patent application filed on May 17, 1985 under No. 85 07 581, corresponding to the U.S. application Ser. No. 863,283, filed on May 15, 1986) and make the use of the above-mentioned catalysts difficult.

The new catalysts according to the present invention only need to be conditioned under hydrogen and/or under reactive gases in a simple manner. Moreover, these new catalysts generally have a reduced transitory methanation, giving them a positive advantage in industrial use and exploitation security.

SUMMARY OF THE INVENTION

It has now been found that highly pure alcohol mixtures can be obtained with catalysts of improved activity and stability, whose use is simpler than the prior art catalysts and which catalysts have a long life time.

The catalysts used according to the invention in the synthesis of alcohol mixtures from hydrogen and carbon oxides ($CO, CO_2$) are essentially formed of the following elements: copper, cobalt, zinc, at least one metal A selected from the group formed of alkali metals and alkaline earth metals, and optionally zirconium and/or at least one metal M and/or at least one metal N as hereinafter defined.

These catalysts are essentially free of aluminum, chromium, iron, vanadium and manganese, i.e. none of these metals is present therein, except only as impurities which may originate from the starting reactants and/or the apparatus used during their preparation, usually in a proportion of less than 0.1% by weight and preferably in a non-detectable amount.

In the catalysts used in the process according to the invention, metal M is selected from the group consisting of scandium, yttrium and rare earth metals of atomic numbers from 57 to 71 inclusive. Metal M is preferably selected from the group formed of lanthanum, cerium, praseodymium and neodymium.

In the catalysts used in the process according to the invention, metal N is selected from group VIII nobel metals (rthenium, rhodium, palladium, osmium, iridium and platinum). Metal N is preferably selected from the group formed of rhodium, palladium and platinum.

The amount by weight of the different metals present in the catalyst, in proportion to the total weight of these metals, is given in the following table.

| Metal | Wide Range | Preferred Range | More Preferred Range |
| --- | --- | --- | --- |
| Cu | 15–55 | 20–45 | 20–45 |
| Co | 5–25 | 8–20 | 8–20 |
| Zn | 15–70 | 20–65 | 20–65 |
| Zr | 0–55 | 0–45 | 0–45 |
| Zn + Zr | 15–70 | 20–65 | 20–65 |
| Metal A | 0.01–5 | 0.05–3.5 | 0.05–3.5 |
| Metal M | 0–20 | 0–20 | 0.1–15 |
| Metal N | 0–1 | 0–1 | 0.01–0.8 |

Metals M and/or N may be absent from the catalysts according to the invention. When metal N is absent and metal M is present, the latter will be preferably present in such an amount that its content by weight be from 0.1 to 15% and, similarly, when metal M is absent and metal N is present, the amount of the latter will be preferably that corresponding to a content by weight from 0.01 to 0.8%.

Metals M and/or N, when both present, will be preferably in such amounts that the metal M content be from 5 to 15% by weight and the metal N content from 0.02 to 0.8% by weight, the proportions of the other metals remaining within the above-mentioned wide or preferred range.

Furthermore, inside the above-mentioned composition ranges by weight the relative atomic proportions of the different metals must be within the wide, preferred or more preferred ranges indicated in the following table:

| Atomic Proportions | Wide Range | Preferred Range | More Preferred Range |
| --- | --- | --- | --- |
| Cu/Co | 0.2:1 to 5:1 | 0.5:1 to 3.5:1 | 1:1 to 3:1 |
| (Zn + Zr)/Co | 0.5:1 to 8:1 | 1:1 to 5.5:1 | 1.2:1 to 5:1 |
| Zn/(Zn + Zr) | 0.05:1 to 1:1 | 0.1:1 to 1:1 | 0.3:1 to 1:1 |

The preferred catalytic formulas are:
1. $Cu + Co + Zn + I_A$
2. $Cu + Co + Zn + Zr + I_A$
3. $Cu + Co + Zn + VIII$ noble metal $+ I_A$
4. $Cu + Co + Zn + Zr +$ rare earths $+ I_A$
5. $Cu + Co + Zn + Zr +$ rare earths $+ VIII$ noble metal $+ I_A$ In these formulas $I_A$ is at least one alkali-metal. Formulas including zirconium are the more preferred.

The zirconium content, in these more preferred formulas, is usually from about 1 to about 45% by weight and preferably from about 2 to about 45% by weight, the sum Zn + Zr and other metals remaining within the above-mentioned wide, preferred or more preferred ranges.

When zirconium is present, the atomic proportion for the (Zn + Zr)/Co ratio is usually from about 1:1 to about 5.5:1, and preferably from about 2:1 to about 5:1 and the atomic proportion for the Zn/(Zn + Zr) ratio is usually from about 0.1:1 to about 0.98:1 and preferably from about 0.3:1 to about 0.98:1.

In order to be both active and stable in the synthesis of higher alcohols having 2 or more carbon atoms in their molecule, and to be selective in the conversion of CO to oxygenated compounds (the by-products whose formation must be reduced to a maximum extent are hydrocarbons), the catalysts according to the present invention must preferably have a good homogeneity of composition and the most active metals, particularly cobalt, must be uniformly distributed among the elementary catalyst particles.

The best results, in terms of selectivity and conversion of CO to oxygenated compounds and particularly to higher alcohols, are obtained with catalysts whose variation of the zinc/cobalt atomic ratio, and optionally of the zirconium/cobalt atomic ratio when zirconium is present, is lower than 15% and preferably lower than 10% of the average value of said ratio, at the scale of 50 Å (5 nanometers).

In order to obtain homogeneous catalysts, a solution (homogeneous by definition) containing copper, cobalt, zinc and optionally zirconium, optionally with at least one metal M and/or optionally at least one metal N, is first prepared and then converted, by a complexing reaction or a coprecipitation reaction, to a solid substance, called a catalyst precursor, having a good homogeneity of composition.

Cu, Co, Zn, optionally zirconium and optionally M and/or N metals are used as soluble compounds, preferably soluble in acid medium, although amminated complexes (soluble in ammonia medium) or copper, cobalt, zinc and of certain metals M and N may also be used in addition to the alkaline and/or ammoniacal coprecipitation reactant.

Examples of such compounds are soluble oxides, hydroxides, carbonates, hydroxycarbonates, soluble in acid medium (e.g. $CuCO_3$—$Cu(OH)_2$, $Co(OH)_2$, $ZnCO_3$—$Zn(OH)_2$, $Zr(OH)_4$, nitrates, oxalates, tartarates, citrates, acetates, acetylacetonates or anionic combinations such as oxalatocobaltate, soluble zirconates; among the soluble salts, nitrates are mostly used.

Metal A may be added at any one of the unitary steps of manufacture. Its addition, for example to the starting solution, may be followed with the addition of at least one complexing agent and with a drying and a roasting step. It is also possible to use a carbonate, bicarbonate and/or a hydroxide of at least one metal A, to prepare the catalyst precursor by coprecipitation with the metal A compound and a solution containing the other metals, Cu, Co, Zn and optionally Zr and/or M and/or N, and to control the amount of metal A in the coprecipitate by controlling further washings, but it is sometimes preferable, after coprecipitation and dealkalization by thorough washing, to mix the precipitate, which may be previously dried, with a controlled amount of a solution of metal A soluble salts, or to thermally activate the precipitate of Cu, Co, Zn and optionally Zr and/or M, and/or N metals and then to add at least one alkali and/or alkaline earth metal A by mixing, as above.

For the manufacture of these catalyst masses, it is essential to use preparation techniques giving a product composition as homogeneous as possible and avoiding the segregation of the different elements during the unitary steps of manufacture.

Preferred methods of manufacture of homogeneous catalytic masses giving homogeneous catalysts, both active and selective for producing higher alcohols, and giving rise to the lowest possible formation of hydrocarbons, are described hereinafter. By these methods the desired homogeneity can be maintained during the manufacturing steps.

A preferred method, already disclosed, as early as 1968, by the applicant, in the French patent application Nos. 1,604,707 and 2,045,612, involves preparing a solution containing Cu, Co, Zn, optionally with Zr and/or M and/or N metals and also optionally with at least one metal A, and then adding at least one compound suitable for the formation of complexes, preferably selected from:

organic acids containing two or more acid groups, for example oxalic, malonic, succinic or glutaric acids,
acid-alcohols, for example glycolic, lactic, malic, tartaric or preferably citric acids,
amino acids, for example aminoacetic acid, alanine or leucine; alkanolamines, for example monoethanolamine, diethanolamine, triethanolamine, in a proportion of about 0.5 to $2COO^-$ or $>-NH$ gram-equivalents per gram-equivalent of metals.

The obtained solution is evaporated under vacuum (for example in a rotary evaporator) so as to obtain a solution having a viscosity of at least 1 Pa.S, which is then transferred into a vacuum oven at a temperature from about 60° to about 120° C. and dried until the water content be reduced to less than 10% by weight. The obtained transparent, vitreous mass, homogeneous and amorphous in X-ray diffraction, is then thermally activated under nitrogen or in the presence of an oxygen-containing gas, for example within a range of about 300°–600° C. for a sufficient time to reduce the volatile matter content to less than 10% and preferably less than 6% by weight.

After thermal activation, a controlled amount of metal A may be optionally added to the activated product, according to the operating mode described hereinafter.

Another preferred mode of manufacture consists of preparing, by at least one coprecipitation reaction, an homogeneous hydrated precursor containing Cu, Co, Zn and optionally Zr and/or M and/or N metals. The coprecipitation reaction consists of reacting, under hereinafter defined operating conditions, a solution of soluble salts of Cu, Co, Zn, optionally Zr and/or M and/or N metals, with a solution of carbonate and/or hydrogenocarbonate (bicarbonate) and/or hydroxide of alkali metals, preferably sodium and/or potassium and/or ammonium, so as to obtain a coprecipitate which, after subsequent washing, forms the homogeneous hydrated precursor.

Any technique and apparatus disclosed in the prior art may be used or applied for performing the invention; for example, it is possible to add the solution of salts of Cu, Co, Zn and other metals into the alkaline solution, or the reverse. Preferably, the two solutions will be added simultaneously, their flow rates being controlled by the pH measured in the reaction zone, into a reactor comprising an efficient stirring system. Preferably, the two solutions will be contacted in the zone of maximum turbulence, defined by the volume surrounding the stirring apparatus inside the reaction volume.

The average residence time, expressed in minutes and defined as the ratio of the reactor volume, expressed in liters, to the total volume flow rate (liters/minute) of the solutions fed to said reactor, may vary from 0.1 to 600 minutes. The reaction may be conducted either in a reactor operated continuously (at stationary concentration and other conditions), whose useful volume may vary from a few $cm^3$ to about 50 liters, when the residence time ranges from 0.1 to 15 minutes and wherefrom the reaction product is continuously recovered (optionally matured in another reactor), then conveyed for example onto a press filter or onto a rotary filter where it is washed, or in a batchwise operating reactor, where the residence time is at least 30 minutes, preferably at least 60 minutes, where the reactants are fed continuously, without corresponding recovery of the reaction product, and where the reaction product remains in the presence of the continuously introduced reactants. This type of reactor, whose volume (taking into account the concentration specifications of the used solutions and the catalyst amounts to prepare) varies from about one liter to about 1000 liters or more, operates at variable concentrations, the other operating conditions remaining constant during the precipitation itself. This mode of reaction is more adapted to the preparation of crystallized compounds, whereas the reactor operating continuously is more adapted to the preparation of compounds which are amorphous in X-ray diffraction.

A preferred embodiment of the invention consists of reacting a solution of soluble salts of Cu, Co, Zn, optionally with Zr and/or M and/or N metals, brought to a temperature ranging from 0° to 30° C., containing at least one gram-atom of all the metals ($Cu+Co+Zn+Zr+M+N$) per liter, with a solution of carbonate and/or hydrogenocarbonate (bicarbonate) and/or hydroxide, preferably of sodium and/or potassium and/or ammonium containing at least 2 gram-atoms of alkali cations and/or ($NH_4^+$) ammonium per liter, the coprecipitation reaction being conducted at 0°–30° C., the pH, measured in the reaction volume, being set at $7\pm1$ pH units and the residence time of the mixture (coprecipitate + mother liquors) in the reaction volume being at most five minutes.

An homogeneous hydrated mixed hydroxycarbonate, amorphous in X-ray diffraction, is thus obtained, giving by X-ray diffraction and goniometric recording a "flat" diagram. This product is then washed so as to reduce its content of alkali metals or ammonium (expressed in proportion of the total weight of metals) to 0.05–5%, preferably 0.09–3.5% by weight, so as to obtain, after final thermal activation, a concentration of metals A at most equal to that desired for the catalyst ready for use.

For this purpose, the dealkalinization known in the art, particularly those disclosed by the applicant in the French patent application No. 2,558,738 (corresponding to the U.S. application Ser. No. 695,021 filed on Jan. 21, 1985) may advantageously be used.

Another preferred embodiment of this invention comprises reacting at a temperature of at least 30° C., preferably at least 50° C., and more preferably at least 70° C., a solution of soluble salts of Cu, Co, Zn, optionally Zr and/or M and/or N metals, at a total concentration of at most 1 g.at. of metals per liter, e.g. from 0.1 to 1 g.at. of metals per liter, with a solution of carbonate and/or hydrogenocarbonate and/or hydroxide, preferably of sodium and/or potassium and/or ammonium at a total concentration of at most 2 g.at. (e.g. from 0.1 to 1.5 g.at.) of alkali metals and/or $NH_4^+$ per liter, the coprecipitation reaction being conducted at a pH of 7±1 pH units and the residence time in the reaction medium being at least 2 minutes. A hydrated mixed hydroxycarbonate, homogeneous, at least partly crystallized, is thus obtained.

The crystallized compound may then be optionally matured, for example at a temperature from about 15° C. to about 100° C. under atmospheric pressure or between about 100° and about 250° C. in an autoclave operating under pressure, for 15 minutes to 5 hours, in the presence of its mother liquor or of its washing waters. During this maturation step, the pH is generally increased up to a pH value at most 1.5 pH unit above the precipitation pH. It is observed that, unexpectedly, this maturation treatment improves the crystallinity and/or increases the size of the crystallites of the crystallized hydrated precursor.

The maturation, when the precipitation is performed batchwise, may be conducted in the same reactor, after stopping the feed of reactants. When the precipitation is performed continuously, the precipitate, obtained under stationary conditions (temperature, concentrations, pH, feed velocity of the reactants may be recovered and matured, after optional washing in another reactor or still in an autoclave.

Preferably, for the preparation of crystallized mixed hydroxycarbonate, the reaction temperature will be at least 70° C. and the pH 7±0.3 pH units, the concentration of the solution of Cu, Co, Zn, M and N metal salts will range from 0.1 to 0.6 g.at. of metals per liter and that of alkali metals and/or ammonium ion from 0.2 to 1.2 g.at. of alkali metals and/or ammonium per liter, the reaction time being at least 5 minutes.

After precipitation and optional maturation in the mother liquors, the crystallized precipitate in washed, so as to reduce its metal A content (expressed as the weight of metal A in proportion to the total weight of the metals) to 0.01–0.4% by weight and more preferably to 0.05–0.2% by weight, then optionally matured in the washing waters. The washing may also be performed in order to reduce the metal A content, e.g. to 0.09–3.5%, for example when no further alkalinization is desired. Another preferred mode of preparation of the catalysts used in the process according to the invention, particularly when the catalyst contains zirconium and optionally at least one metal M, consists of performing a two-step precipitation and then admixing the two coprecipitates so as to form a substantially homogeneous dispersion. This preparation comprises the following steps of: (a) preparing, by at least one of the above-described coprecipitation procedures, a hydrated precursor containing copper, cobalt, at least a part of the zinc (as compared with the total zinc amount whose introduction into the catalyst to be prepared is desirable) and optionally at least one metal N; (b) washing with water the at least partly crystallized hydrated precursor obtained in step a) so as to obtain a product containing less than about 0.2% by weight of alkali metals in proportion to the total weight of the metals; (c) preparing, in the above-described manner, by hot coprecipitation, i.e. at a temperature higher than about 30° C., preferably higher than 50° C. and more preferably higher than 70° C., a hydrated precursor containing zirconium, optionally the necessary zinc complement and optionally at least one metal M, these various metals being supplied from at least one of the above-mentioned soluble compounds, the coprecipitating agent being at least one compound of ammonium cation (hydroxide, carbonate, bicarbonate). The coprecipitation pH ranges from about 6 to 8 pH units; after coprecipitation, the hydrated compound containing the above-mentioned metals may optionally be matured in the above-mentioned operating conditions. After precipitation and optional maturation in the mother-liquors, the precipitate, containing zirconium, optionally a part of the zinc and optionally at least one metal M, is washed (step d) with water so as to reduce its nitrogen content ($NH_4^+$ and optionally $NO_3^-$), to a proportion of the total weight of metals lower than 3% and preferably lower than 1% by weight.

The two washed coprecipitates, obtained as abovementioned, are then admixed (step e) in an apparatus adapted to form the most possible homogeneous dispersion of the two products in each other. The dispersion may be measured by a Castaing microprobe or by X-ray microanalysis with scanning transmission electron microscope (STEM). The best results are obtained with a substantially homogeneous dispersion at a scale of 0.01–0.1 (micron).

The substantially homogeneous dispersion of the two coprecipitates, resulting from their thixotropic properties, is obtained by subjecting the mixture to sufficiently high shearing forces, applied to the product through revolving blades, discs, cylinders or by passage through orifices, for example, in Werner, Cowles, Waring, Hobart, Hochmeyer, Rousselle mixers and in certain roller mixers. After stopping of the shearing mixing, no settling and/or segregation must be observed.

The drying of the homogenized mixed product may be achieved by any known process; it can be performed, for example, by spray-drying. A substantially homogeneous product is obtained as calibrated powder containing about 60 to about 80% by weight of oxide equivalents. The product may also be dried in an oven, for example at a temperature from about 50° to about 150° C., under air scavenging conditions, so as to reduce, if necessary, its potential oxide content to about 60–80% by weight. It is recommended to avoid the stagnancy of the precipitate in the presence of steam partial pressures close to the saturing vapor pressure at the drying temperature. Such treatments may result in a partial dehydration of the precipitate with crystallization of the copper oxide to large crystallites. A combined spray-dying followed with a drying in a stove is also possible.

Detailed examples of this preparation technique are given in U.S. Pat. No. 4,552,861 to the applicant.

After precipitation and washing according to one of the previously described preparation procedures, an homogeneous hydrated precursor (crystallized or amorphous) is obtained which contains about 10–30% by weight of oxides when amorphous and about 15–60% by weight when crystallized.

In this amorphous or crystallized precursor, the metal distribution is homogeneous and the relative Zn/Co and optionally Zr/Co atomic ratios vary by less than 15% and preferentially by less than 10%, at a 5 nm scale.

In the mixed precursors obtained by precipitation in two separate steps and which are formed by juxtaposition of homogeneous particles of sizes ranging from about 3 to about 100 nm and of different compositions, the zinc/cobalt and optionally zirconium/cobalt ratios will be measured with high resolution on the cobalt-containing specific particles.

Similarly, particles containing no cobalt are homogeneous with each other.

A first mode of optional addition of the one or more metals A (at least one alkali and/or alkaline-earth metal) consists of contacting the hydrated precipitate with a solution containing the one or more metals A and then to vigorously stir so that, after suspension of the precipitate in the alkaline solution, followed with an optional maturation and/or filtration, the latter contains at least one of the above-mentioned metals A in a convenient proportion.

The drying of the suspension of precipitate and metals A in solution, after optional maturation, may for example be achieved by spray-drying and/or in a stove. The obtained dried alkalized precipitate, calibrated powder, consists of hollow spheroids (cenospheres) having a diameter of 3–700 microns and an homogeneous composition, containing from about 60 to about 85% by weight of oxides, either amorphous, when originating from an amorphous hydrated precursor, or crystallized, when originating from a crystallized product.

The precipitate may also separated from the alkalizing medium by filtration, then optionally matured, then dried, for example by spray-drying and/or by drying in oven, so as to reduce its content of oxides to about 65–85% by weight.

Another mode of alkalinization consists of adding at least one metal A as aqueous and/or organic solution which may be admixed with the dried precipitate (amorphous, spray-dried or crystallized). An homogeneous paste is thus obtained which is then dried by any suitable technique, for example as above-stated.

This precipitate is then thermally activated but this activation treatment may also be conducted on a precipitate thoroughly dealkalized by washing (amorphous or crystallized) not yet containing at least one metal A and having the above-mentioned property of homogeneity.

The thermal activation consists of treating the dry precipitate, alkalized or not yet alkalized, at a temperature from about 250° to about 600° C., preferably from about 300° to about 500° C., for a sufficient time, for example at least 0.5 hour, to obtain an homogeneous activated catalyst containing no more than 12% by weight of volatile matters (the volatile matter content is measured for example by activation, in the presence of air, of a given weight of product placed in a boat and roasted at 600° C. for 4 hours).

The thermal activation may be conducted either in the presence of an inert gas of 0–50% oxygen content, thus giving an homogeneous mixed oxide, or in the presence of a reducing medium (mixture of inert gas with reducing gas containing 0.1–100% of reducing gas); the reducing gases, used alone or as mixture, are for example hydrogen or ammonia.

The thermal activation, in a reducing medium in the aggregate, may be conducted either on the dried precursor or on the mixed oxide previously activated, in an oxidizing medium in the aggregate.

After thermal activation, in a reducing medium in the aggregate, the mixed oxide may be partially reduced (by the hydrogen-containing gas) or still partly reduced and nitrided (by the ammonia-containing gas).

The thermally activated and then optionally crushed catalyst may be optionally contacted thereafter with an aqueous or organic solution of at least one metal N, so as to disperse said metal substantially uniformly and to obtain, after drying and thermal activation as above, a catalyst wherein said metal is well dispersed (the dispersion may be measured for example by chemisorption of reactive gases CO, $H_2$, on said metal). Except for halides and sulfates, all the soluble salts, for example nitrates, acetylacetonates, as well as complexes, for example nitrosamminated, amminated, carbonylated complexes, can be used.

The homogeneous hydrated precipitate (amorphous or crystallized) thoroughly dealkalized, dried so as to reduce its volatile matter content to less than 35% by weight and then thermally activated, optionally impregnated with at least one metal N, may be finally alkalized as follows: the homogeneous product resulting from the thermal activation is crushed so to obtain a powder of particle size at most equal to 0.2 mm; then the alkalizing agent (at least one metal A) is added, for example by mixing said product with an aqueous and/or organic solution containing at least one compound of at least one metal A in above-mentioned proportions.

After addition of the alkalizing agent, the paste may optionally be shaped by extrusion (by this way, after drying and activation, extrudates having good mechanical properties can be obtained) and then dried by any known technique. Before drying it may be advantageous to perform a maturation step in the surrounding air for a sufficient time to reduce the water content of the product to less than 25% and preferably to less than 20% by weight.

Another mode for adding the alkalizing agent with simultaneous shaping involves placing the above-mentioned powder in a bowl-granulating turbine, then to spray onto the powder, driven in a rotary motion, the aqueous or organic solution containing the alkalizing agent. By this way, calibrated balls (e.g. from 2.4 to 5 mm) are obtained which, after optional maturation, drying and thermal activation, give a homogeneous activated catalyst having good mechanical properties.

Another process including the combination of the alkalinization with the shaping step involves making a suspension containing the activated catalyst having a catalyst content of about 30–60% by weight and at least one metal A and then, optionally after maturation, of performing a flash roasting step in a sprayer operating in the presence of a combustion gas containing less than 1 mg of sulfur per $N.m^3$ and having an input temperature of at least 500° C. By this way, microspheres of 2 to 700 microns are obtained which may be optionally used in a liquid phase process with catalyst circulation.

During at least one of the unitary steps where the hydrated precursor or the dried hydrated precursor, or the activated catalyst is contacted with at least one liquid phase, it may be advantageous to subject the mixed medium (solid+liquid) to ultrasound, so as to complete their interaction, to at least partly fragment of the solid and/or to at least partly control the modification of the crystalline state.

The ultrasound treatment may obviously be coupled with the coprecipitation operation; then the reactor contains at least one ultrasound generator which is actuated during the unitary coprecipitation step and/or during the optional maturation step.

This treatment may also be advantageously applied to suspensions comprising at least one coprecipitated, hydrated precursor, in the optional presence of at least one alkali and/or alkaline-earth metal A; it may improve the dispersion and/or the homogeneity and/or facilitate a subsequent drying when performed by spraying.

In laboratory, for example, such generators as UL-TRASONICS inc. (USA) of the types referenced W 220 F, W 225 R, whose radiation frequency corresponds to 20 KHz (20,000 cycles per second), can be used at a power of 10 to 200 watts. This radiated power is sufficient to treat a volume of products of at most 15 liters. More powerful apparatuses may advantageously be used for treating larger volumes.

The alkalized catalyst, prepared as above stated (homogeneous paste, homogeneous extrudates, homogeneous balls, homogeneous microspheres) optionally matured, optionally dried, if necessary, to reduce its volatiel matter content to less than 35% by weight and preferably to less than 25% by weight, is finally thermally activated in the conditions and in the presence of the above-mentioned gaseous reactants.

However, this second thermal activation will be preferably conducted between about 300° and about 450° C., for a sufficient time to reduce the volatile matter content of the product to less than 12% by weight.

When the alkalized catalyst, thermally activated in the above-mentioned conditions, has not yet been shaped, it will be shaped as follows:

The homogeneous product, thermally activated, is crushed, for example to a particle size below 0.5 mm, admixed in a proportion of 0.5–5% of its weight with at least one pelletizing adjuvant selected from the group formed of graphite, stearic acid, stearates and optionally a porosity adjuvant selected from cellulose or cellulose-containing powders of vegetable origin, ammonium nitrate and carbonates, combustible textile fibers, naphthalene, and then pelletized to solid cylinders of 3–6 mm diameter or to toric cylinders of 3–6 mm external diameter, 1–4 mm internal diameter and 2–6 mm height.

The catalyst, shaped by pelletizing, will be optionally subjected to at last thermal activation in the above-mentioned operating conditions.

The thermally activated catalyst, ready for use, consists of a very homogeneous association of oxides (optionally some of them may be reduced, at least partly, when at least one thermal activation has been conducted in a reducing medium, in the aggregate). In this association of very homogeneous oxides, the metals and particularly cobalt, zinc and zirconium when the catalyst contains it are distributed very homogeneously at the scale of 5 nm and the relative variations of the atomic ratios Zn/Co and optionally Zr/Co are lower than 15% and preferentially lower than 10%. The specific surface of said catalysts varies from about 20 to about 300 $m^2.g^{-1}$. The thermal activation, when conducted in the presence of at least one alkali and/or alkaline-earth metal A, at a temperature of at least 350° C., may produce the recrystallization of individual particles of copper oxide CuO (tenorite) visible in X-ray diffraction, without however modifying the dispersion of cobalt with respect to the other above-mentioned metals Zn, Zr, M, N and A.

The parameters for use of these catalysts for manufacturing alcohols are usually the following:

The catalyst, charged into the reactor, is first reduced by a mixture of inert gas (e.g. nitrogen) with at least one reducing compound selected from the group formed of hydrogen, carbon monoxide, alcohols and $C_1$ and $C_2$ aldehydes, the molar ratio "reducing compound/reducing compound+inert gas" being from 0.001:1 to 1:1.

The reduction temperature generally varies from 100° to 350° C., preferably from 130° to 320° C. The total pressure is usually from 0.1 to 5 MPa and preferably from 0.2 to 2 MPa; the hourly volume velocity is generally from 50 to 10,000 hours$^{-1}$ and preferably from 100 to 5000 hours$^{-1}$ (at N.T.P.).

More preferably, the reduction will be conducted for example at a temperature from about 150° to about 300° C., in the presence of the above-mentioned reducing mixture and with a molar ratio "reducing gas/reducing gas+inert gas" from 0.001:1 to 0.1:1 and preferably from 0.005:1 to 0.05:1, the reduction temperature being progressively increased (e.g. by 20° C. steps) and each temperature increase being followed with an isothermal stage, at stationary temperature, for a sufficient time to equalize the reducing gas concentrations at the reactor input and output (thus showing that the reduction at the temperature of said stage is complete).

The catalyst reduction may also be conducted in the liquid phase when the subsequent alcohol synthesis is conducted in the liquid phase. The operating conditions remain unchanged, but the rate of temperature increase and/or the reducing gas concentration in the gas mixture may be higher, while remaining within the above-mentioned ranges.

The catalyst, reduced as above-stated, may finally be contacted with the synthesis gas ($CO+H_2+CO_2$). As known in the art, said contact must be progressive. The initial operating temperature is generally higher than 210° C. and preferentially higher than 230° C.

The operating conditions of pressure and hourly volume velocity are defined hereinafter.

The proper reaction of alcohol synthesis is conducted in the following operating conditions:

The total pressure is usually from 2 to 25 MPa and preferably from 5 to 15 MPa.

The ($H_2+CO+CO_2$) partial pressure will generally be lower than the total pressure, this difference resulting from the accumulation, by recycling of unconverted gases, of inert gases ($CH_4$, $N_2$, rare gases) contained in the added gas feed, as well as from the accumulation of the reaction hydrocarbon by-products (essentially $C_1$, $C_2$, $C_3$ hydrocarbons).

The ($H_2+CO+CO_2$) partial pressure will usually range from 2 to 15 MPa, preferably from 5 to 12 MPa.

As stated below, the average $H_2/CO$ molar ratio in the reaction zone, defined as the average of the ratios at the input and at the output of the reactor, is from 0.1:1 to 4:1, preferably from 0.2:1 to 3.5:1, the average temperature in the reactor being from 250° to 350° C., preferably from 260° to 320° C.

The hourly volume velocity (expressed by NTP volume of gaseous mixture per volume of catalyst and per hour) usually ranges from 1,000 to 40,000 h$^{-1}$ and preferably from 2,000 to 20,000 h$^{-1}$.

The catalyst may be used as fine calibrated powder (10 to 700 microns) or as particles of 2 to 10 mm equivalent diameter, in the presence of a gas phase or of a liquid (in the operating conditions) phase and a gas phase. The liquid phase may consist of one or more hydrocarbons having at least 5 and preferably at least 10 carbon atoms.

In this embodiment, the surface velocities of the gas and the liquid, in the prevailing temperature and pressure conditions of the process, are preferably of at least 1.5 cm/sec. and more preferably of at least 3 cm/sec. The surface velocity is defined as the ratio of the volume flow rate to the cross-sectional area of the reactor when empty of catalyst.

The synthesis of alcohols being a very exothermic reaction, it is essential that the operating conditions (temperature, pressure, composition of the reaction mixture, volume velocity per hour-VVH) be so adjusted as to limit the chemical conversion of the reaction mixture (CO+H$_2$) in the presence of the above-mentioned catalysts and accordingly the resultant thermal effects.

For this reason, it may be advantageous to limit the conversion (per run) of carbon monoxide (CO) to about 5–25% and, after condensation of the liquids produced by the reaction, to recycle at least partly the unconverted gases so as to convert, as a whole, 85 to 95% of the CO contained in the added gas.

This operating manner is known and used in the art for the industrial process of methanol synthesis from CO+CO$_2$+H$_2$.

The reactors used for the synthesis of alcohols, in the presence of the catalysts according to the invention, may be either isothermal (generally the reactor is of multitubular type, the catalyst being placed inside the tubes and the reaction heat being transferred to a suitable thermal fluid) or adiabatic.

Any adiabatic reactor, wherein a maximum amount of catalyst can be placed in a minimum total volume, and simultaneously the temperature increase in the catalyst particles and/or bed is reduced and the pressure drop in the reactor limited, can be used. These reactors may contain one or more catalyst beds.

The flow of synthesis gas in the reactor may be axial or radial or mixed. A portion of the synthesis gas and/or of the reaction gaseous products, after convenient cooling, may be introduced between the catalyst beds (quench cooling). The reaction heat may also be removed conventionally by intermediary exchangers, placed either outside or inside the reactor.

The synthesis reaction may be conducted with one or more reactors in series and/or in parallel. With an arrangement in parallel the reaction products may advantageously be intermediately condensed before admission of the unconverted gas into the next reactor. In the synthesis reaction producing methanol, higher alcohols, water and, to a lesser extent, hydrocarbons, a portion of the CO may be converted to CO$_2$ according to the following CO conversion reaction (balanced):

$$CO + H_2O \rightleftharpoons CO_2 + H_2$$

The catalysts object of the present invention also have a very good activity in the conversion of carbon monoxide according to the above-mentioned reaction.

In order to limit the amount of water, formed together with the produced alcohols, it may be advantageous to remove a part of the CO$_2$ formed during the reaction (for example by decarbonatation with a suitable CO$_2$ solvent medium) after condensation of the liquids and before recycling, at least partly, the above-mentioned gas.

The water-conversion of CO is a balanced reaction:

$$CO + H_2O \rightleftharpoons CO_2 + H_2$$
$$K_{(T)} = \frac{P_{CO_2} \cdot P_{H_2}}{P_{CO} \cdot P_{H_2O}}$$

Accordingly, at a temperature T, the water partial pressure $P_{H_2O}$ at the reactor output will depend on the CO$_2$ partial pressure, on the H$_2$/CO ratio and decrease as these two values will be lower;

$$P_{H_2O} = \left(\frac{H_2}{CO}\right) \cdot \frac{P_{CO_2}}{K_T}$$

Since otherwise the constant $K_T$ increases rapidly as soon as the temperature decreases, the catalysts will advantageously have to be particularly active when operating at low temperatures.

Although the catalysts according to the invention may be used in the presence of synthesis gas (H$_2$+CO+CO$_2$) containing up to 15%, preferably at most 10% by volume of CO$_2$, it may be advantageous to limit the average CO$_2$ concentration to 0–5% and preferentially to 0.1–3% by volume in the reactor, so as to convert a maximum amount of the water formed together with the alcohols and/or the hydrocarbons and to simplify the alcohol dehydrating procedure. The produced raw alcohols generally contain from 0.1 to 10% by weight of water, more particularly from 0.5 to 5% by weight.

From the same purpose, it may be also advantageous to adjust the H$_2$/CO molar ratio in the reactor within the range from 0.2 to 3.5 and more particularly from 0.5 to 2.8.

EXAMPLES

The following examples describe different aspects of the invention for illustration purpose but must not be considered as limiting the scope thereof.

The preparation of catalysts A to J, whose characteristics are reported in table I, is first described. The filling density is determined for a reactor having an inner diameter of 2.5 centimeters.

CATALYST A 193.3 g trihydrated copper nitrate (0.8 g.at Cu), 174.62 g of hexahydrated cobalt nitrate (0.6 g.at. Co), 267.27 g of dihydrated zirconyl nitrate (1.0 g.at. Zr) are dissolved into water in the presence of 0.3 liter of pure nitric acid (d=1.38) and 148.74 g of hexahydrated zinc nitrate (0.5 g.at Zn). The solution (solution A, 0.48 g.at./l) is diluted to 6 liters.

Separately, 640 g of anhydrous disodium carbonate are dissolved into 10 liters of water (solution B, 1.2 g.at. Na/liter).

The two solutions, brought to 75° C., are simultaneously introduced into a 2.0 liter reactor, containing 1.5 liter of water brought to 75° C.; this reactor is provided with an overflow; the flow rates of the two solutions are controlled by the pH, measured in the turbulence zone of the stirring turbine (STARO turbine). The precipitation time is 1 hour 30 minutes and the average residence time 12.4 minutes; the pH varies from 6.95 to 7.04 pH units. The precipitate, matured for 1 hour at 40° C. in the presence of its mother liquors, is then washed with 36 liters of bi-exchanged water (3 successive washings with 12 liters of water). The washed precipitate contains 28% by weight of oxides and 0.04% by weight of sodium in proportion to the metals. 750 g of washed precipitate (210 g of oxide equivalents) are placed into a HOBBART mixer, admixed with 0.05 l of water containing 1.09 g of dipotassium carbonate (0.016 g.at. K) and 2.44 g of disodium carbonate (0.046 g.at. Na). The mixture is mixed for 2 hours, then matured 10 hours at 25° C. before spray-drying (output temperature: 150° C., average residence time t=0.9 second). The obtained product, which contains 77% by weight of oxides, is thermally activated in air at 350° C. for 4 hours, admixed with 2% by weight of natural graphite and then pelletized to cylinders of 4 mm diameter and height. After thermal activation (300° C., 2 hours in nitrogen), 190 g of pellets is obtained whose filling density is 1.12 kg/l.

CATALYST A1

This catalyst is prepared in the same operating conditions as those described for the preparation of catalyst A. 150 g of oxides are thus prepared before alkalinization. The alkalinization, performed with an aqueous solution of disodium carbonate, is followed with a hydrothermal maturation in a closed vessel (T=60° C., t=4 h); then the product is dried, activated, pelletized and reactivated, as above for the preparation of catalyst A. 80 g of pellets (3.5×4 mn) of 1.15 kg/l filling density is thus obtained.

CATALYST B 12 liters of a solution containing 410.75 g of trihydrated copper nitrate (1.7 g.at. Cu), 232.85 g of hexahydrated cobalt nitrate (0.8 g.at. Co), 297.50 g of hexahydrated zinc nitrate (1 g.at. Zn) and 79.45 g of trihydrated cerium hydroxynitrate (0.2 g.at. Ce) are prepared. This solution A contains 0.308 g.at. of metals per liter; it is preheated at 75° C.

Separately, 549 g of disodium carbonate are dissolved in 17 liters of bi-exchanged water, preheated at 70° C. (solution B, 0.61 g.at. Na/liter).

In a 50 liter reactor containing 5 liters of bi-exchanged hot water (70° C.) provided with external heating means, stirring means (helix, 700 r.p.m.) and with an ultrasound generator W 220 F (absorbed power of 150 watts) and with a pH regulation with pH-controlled flow rates, the two solutions are simultaneously introduced; the operation lasts 3 hours. At the end, the precipitate is cooled, then matured for 5 hours at 40° C. and finally washed on a laboratory press-filter.

The final alkali content of the washed precipitate is 0.025% by weight, in proportion to the metals. The washed product is crystallized, then homogenized; it contains 33% by weight of oxides.

After mixing as herebefore for the preparation of catalyst A, but with 3.045 g of $K_2CO_3$ (0.045 g.at. K) and 0.705 g of $Rb_2CO_3$ (0.006 g.at. Rb) in 0.1 liter of water, for 30 mn, and maturation for 60 hours at 15°-22° C., the alkalized precipitate is spray-dried (average residence time: 1.5 second; output temperature: 130° C.), thermally activated (T=320° C., t=10 hours), then pelletized after addition of 1.5% of magnesium stearate. After the last thermal activation (T=350° C., t=1 hour), 302 g of 4×4 mm pellets having a filling density of 1.18 kg.l$^{-1}$ is obtained.

CATALYST C

A mixed oxide of formula $Nd_{0.2}Zr_{0.6}O_{1.8}$ is first prepared. 0.2 mole of hexahydrated neodymium nitrate (87.7 g) and 0.6 mole of dihydrated zirconyl nitrate (160.36 g) are dissolved in 2 liters of water, in the presence of 0.15 l of pure nitric acid (d=1.38) and heated at 85° C.

0.36 kg of a diammonium carbonate solution $(NH_4)_2CO_3$, containing 30% by weight of crystallized salt, are diluted in 2 liters of cold water. The solution is then heated to 65° C. Simultaneously, the two solutions are introduced into a reactor operating continuously (according to the method described for catalyst A). The average residence time is 20 mn; the pH varies from 6.5 to 6.8 pH units; the product is directly washed 3 times with 18 liters of bi-exchanged hot water.

530 g of wet precipitate (107 g of oxides), containing less than 0.3% by weight of nitrogen, is obtained.

Separately, 223.44 g of catalyst of formula $Cu_1Co_{0.4}Zn_{1.4}O_{2.8}$, containing 35.57% Cu, 13.19% Co and 51.24% Zn in proportion to the metals, is prepared according to the procedure described for catalyst A and up to the maturation step after washing. 860 g of washed precipitate (0.04% Na in proportion to the metals) containing 223.44 g of oxides is obtained.

The two precipitates (Nd, Zr) and (Cu, Co, Zn) are placed in a WARIG BLENDER mixer and stirred for 3 hours at room temperature. The obtained thixotropic solution is then treated with 0.1 liter of a solution containing 8.96 g of $Na_2CO_3$ (0.169 g.at. Na) and 0.740 g of $Cs_2CO_3$ (0.0045 g.at. of Cs), matured under slow stirring for 6 further hours at room temperature, then spray-dried (T=120°-140° C., t=2 seconds).

398 g of homogeneous dried product containing 75% by weight of oxides are obtained. This product, roasted for 5 hours at 400° C., is admixed with 2.5% of natural graphite, then pelletized to toric pellets of 5 mm external diameter and height and 2.5 mm internal diameter. The filling density of the product is 1.05 kg/l.

By examination with Scanning Transmission Electron Microscope (STEM), the catalyst appears as contituted by two different phases, one containing copper, cobalt and zinc in a Zn/Co ratio in the cobalt-containing particles varying from 3.4 to 3.8 and the other containing zirconium and neodymium, also in a very homogeneous distribution. Sodium and cesium are also very homogeneously distributed.

CATALYST D1

314.8 g of trihydrated copper nitrate (1.3 Cu), 145.52 g of hexahydrated cobalt nitrate (0.5 Co) and 357 g of hexahydrated zinc nitrate (1.2 Zn) are dissolved into 2 liters of bi-exchanged water; then 420 g of monohydrated citric acid (2 moles) and finally 1.18 g of dihydrated trisodic sodium citrate (0.012 g.at. Na) are added. After evaporation under vacuum (70° C., 0.01 MPa) for 5 hours, the obtained vitrous substance is crushed and then progressively introduced into a vertical tube heated to 500° C. and scavenged with a dry air steam.

The average residence time is about 1 minute. The divided powder is finally roasted under air scavenging in a batch-type furnace (400° C.—3 hours); compacted, pelletized and again roasted (300° C.—1 hour); 165 g of pellets of 3 mm diameter and height is obtained. Their filling density is 1.35 kg.l$^{-1}$. The specific surface measured by the BET method, is 27 m$^2$.g$^{-1}$.

CATALYST D2

The same amount of the same salts as those used for the preparation of catalyst D1 (except for citric acid and sodium citrate) are dissolved in cold bi-exchanged water; 4.5 liters of solution (0.67 g.at/l) are prepared. Separately, 6 liters of an aqueous solution (20° C.) containing 238.5 g of disodium carbonate is prepared.

The two solutions are mutually contacted in the apparatus described for the preparation of catalyst A. The average residence time in the coprecipitator is 15 minutes; the pH varies from 7.02 to 7.07 pH units. After subsequent filtration, the precipitate is immediately suspended into 12 liters of cold bi-exchanged water (stirring for 30 mn-RAYNORI turbine); the operation is repeated 8 times.

There is obtained (losses being taken into account) 140 g of oxides in the form of a hydrated, amorphous in X-ray diffraction and very homogeneous coprecipitate whose sodium content (residual sodium, ex precipitation) is 0.15% by weight in proportion to the metals.

The precipitate is mixed for 30 minutes (BECKEN mixer with sigmoid blades), then dried in a stove at 60° C. for 5 hours, then at 90° C. for 3 hours and finally at 120° C. for 2 hours. It is then thermally activated in air (420° C.—10 hours), pelletized (addition of 2% of graphite) and reactivated at 320° C. for 2 hours. 120 g of pellets of 3 mm of diameter and height is obtained. The pellets have a filling density of 1.3 kg/l$^{-1}$ and a specific surface of 83 m$^2$.g$^{-1}$.

CATALYST D3

The same salts as for manufacturing catalyst D2 are used. The solution of nitrates (volume=6 liters; concentration: 0.5 g.at/l, T=75° C.) and the sodium carbonate solution (volume=7.5 liters, concentration=1.2 g.at. Na/l, T=75° C.), are reacted in the same reactor as described for the preparation of catalyst A, operating continuously, but at 75° C.; the pH varies from 7.0 to 7.05 pH units and the average residence time is 8 minutes.

After 16 hours of maturation (room temperature) in its mother-liquors, the coprecipitate is washed 3 times with 45 liters (3×15 l) of bi-exchanged water. The washed, homogeneous precipitate is formed of a crystallized phase. Its residual sodium content is 0.025% in proportion to the metals.

This precipitate is mixed with 0.05 liter of a solution containing 0.64 g of disodium carbonate (0.012 g.at. Na), then matured for 12 hours at 35° C. and finally spray-dried and thermally activated for 3 hours at 350° C., pelletized with addition of 1.5% by weight of stearic acid and reactivated for 2 hours at 300° C. 165 g of pellets (3×3 mm) of 1.3 kg.l$^{-1}$ filling density and 106.5 m$^2$.g$^{-1}$ specific surface, is obtained.

CATALYST D4

The preparation of catalyst D3 is repeated, except for the addition of alkali and the maturation before spray-drying. The washed product is hence directly spray-dried, then thermally activated for 3 hours at 350° C.

120.5 g of oxides as a light powder (apparent density 0.1 kgl$^{-1}$) is thus obtained. This powder is mixed in a WARIG-BLENDER apparatus with 0.2 liter of a solution containing 0.64 g of disodium carbonate (0.012 g.at. Na), then dried for 0.1 h in a microwave furnace and finally activated, shaped and reactivated as herebefore described for the preparation of catalyst D3.

153 g of pellets (3×3 mm) having a filling density of 1.23 kg.l$^{-1}$ and a specific surface of 76 m$^2$.g$^{-1}$ is obtained.

CATALYST E

This catalyst is prepared in the same operating conditions as those described for the preparation of catalyst B. Lanthanum and praseodymium are used as nitrates and replace cerium; zirconium is used as dihydrated zirconyl nitrate. 226.8 g of oxides is thus prepared before alkalinization.

The alkalinization, performed with aqueous dipotassium carbonate is followed with a hydrothermal maturation in a tightly closed vessel (T=60° C., t=4 hours), then the product is dried, activated, pelletized and reactivated as hereabove described for the manufacture of catalyst B.

208 g of pellets (3.5×4 mm) having a filling density of 1.23 kg.l$^{-}$ is obtained.

CATALYST F

The operating conditions are the same as for catalyst D4 up to thermal activation (3 hours at 350° C.). 150 g of oxides as an activated product is contacted with 0.6 g of palladium acetate and 0.3 g of rhodium as rhodium III acetylacetonate in alcoholic solution (180 ml of ethanol). After drying under nitrogen at 150° C. and a further roasting step for 3 hours at 350° C., the catalyst is then alkalized, dried, activated, shaped and reactivated as described for the preparation of catalyst D4.

117 g of pellets (3×3 mm) having a filling density of 1.35 kg.l$^{-1}$ and a specific surface of 70 m$^2$.g$^{-1}$ is obtained. This catalyst contains 0.4% Pd and 0.2% Rh in proportion to the oxides, i.e. 0.5% Pd and 0.25% Rh in proportion to the metals.

CATALYST G

Comparative 241.6 g of trihydrated copper nitrate (1 g.at. Cu), 145.52 g of hexahydrated cobalt nitrate (0.5 g.at. Co) and 400.9 g of dihydrated zirconyl nitrate (1.5 g.at. Zr) are dissolved in water in the presence of 0.3 liter of pure nitric acid (d=1.38); the solution (0.5 g.at/l) is diluted to 6 liters.

Separately, 640 g of anhydrous disodium carbonate is dissolved into 10 liters of water (1.2 g.at. Na/liter solution).

The two solutions, brought to 75° C., are simultaneously introduced into a 2 liter reactor containing 2 liters of water brought to 75° C. This reactor is provided with an overflow; the flow rate of the two solutions are regulated by the pH, measured in the turbulence zone of the stirring turbine (STARO turbine). The precipitation time is 1 h 30 minutes and the average residence time 12.4 minutes; the pH varies from 6.95 to 7.04 pH units.

The precipitate, matured for 20 hours at 40° C. in the presence of its mother liquors is then washed with 36 liters of bi-exchanged water (3 washings with 12 liters).

It contains 28% by weight of oxides and 0.08% by weight of Na in proportion to the metals.

The washed precipitate is placed in a WERNER mixer and admixed, under stirring, with 0.1 liter of a solution containing 3.68 g of anhydrous dipotassium carbonate (0.054 g.at. K.). The paste is matured for 10 hours at 40° C., they spray-dried; the average temperature is 120°–140° C.; the drying time is 1 second.

The obtained dry product, containing 77% by weight of oxides, is thermally activated in air at 350° C. for 4 hours, admixed with 2% of natural graphite and then pelletized to cylinders of 4 mm diameter and height.

After thermal activation (300° C., 2 hours, under nitrogen), 200 g of pellets is obtained with a filling density is 1.2 kg/l$^{-1}$.

CATALYST H

Comparative

Catalyst H is prepared according to the operating conditions described for the preparation of catalyst A, with different amounts of the same salts as those used for preparing catalyst A.

The alkalinization is performed only with dipotassium carbonate.

CATALYST I

Comparative

Catalyst I is similary prepared according to the operating conditions described for the preparation of catalyst D4, but with different amounts of the same salts as those used for preparing catalyst D4. The alkalinization is performed with dipotassium carbonate instead of disodium carbonate used for the manufacture of catalyst D4.

CATALYST J

Comparative 5 liters of a solution containing:
244.00 g of trihydrated copper nitrate (1.01Cu)
7.28 g of hexahydrated cobalt nitrate (0.025Co)
38.67 g of hexahydrated zinc nitrate (0.13Zn)
is prepared.

This solution contains 0.233 g.at/l of metals. Separately, 170 g of disodium carbonate is dissolved into 7 liters of bi-exchanged water (solution at 0.46 g.at. Na/liter).

The two solutions, brought to 80° C., are simultaneously introduced into a 2 liter reactor, containing 1.5 liter of water brought to 80° C., and provided with an overflow. The flow rates of the two solutions are regulated by the pH, as measured in the turbulence zone of the turbine (STARO turbine), which is maintained in the range from 6.95 to 7.05 pH units.

The precipitate, matured for 20 hours at 40° C. in the presence of its mother liquors, is then washed with 30 liters of exchanged water (3 washings with 10 liters of water); it contains 30% by weight of oxides and 0.10% by weight of sodium in proportion to the metals.

The alkali is added by mixing (HOBART mixer) the 320 g of washed precipitate with 1.85 g of dipotassium carbonate (0.027 g.at. K.) and 1.85 of dirubidium carbonate (0.016 g.at. Rb) into 0.05 liter of water. The precipitate is mixed for 3 hours and then matured for 10 hours at 25° C. before spray-drying at an average temperature of 110° C., the average residence time being t=1 second. The obtained dry product contains 75% of oxides; it is activated under air, pelletized and activated under nitrogen in the conditions described for the preparation of catalyst A.

80 g of pellets having a filling density of 1.10 kg.l$^{-1}$ is obtained.

TESTS OF THE CATALYSTS

The catalysts of examples A to J have been tested in a pilot unit operating continuously with 50 ml of catalyst. The unit is fed with a synthetic gas mixture in relative proportions of $H_2$, CO, $CO_2$ very close to those measured in an industrial unit; it comprises a partial recycling of the unconverted gases.

Examples 1 to 23, using catalysts A to J, reported in table 3, illustrate the improved performance and stability of the catalysts A to F according to the invention. The performance of catalysts A to F at 2000 hours are reported in table 4 for examples 1, 3, 9 to 12, 14, 16 and 17 conforming with the invention and that of comparison catalysts G and H, in examples 19 and 20. The performance is defined as follows:

Productivity by weight to alcohols r: it is the number of grams of alcohols obtained per hour in proportion of the weight (in grams) of the charged catalyst; it is expressed in hours$^{-1}$(h$^{-1}$).

Productivity by volume to alcohols p: it is the number of grams of alcohols obtained per hour in proportion to the volume (in cubic centimeters) of the charged catalyst; it is expressed in g.cm$^{-3}$h$^{-1}$.

Selectivity by weight to higher alcohols $S_{C_2+OH}\%$: it is the ratio by weight: $100 \times C_2^+OH$ alcohol weight/total weight of formed alcohols.

Selectivity of CO and $CO_2$ conversion to alcohols $S_A$; $C_1OH, C_2OH, C_3OH, C_4OH \ldots C_nOH$ being the number of gram-molecules formed for each alcohol, the number of CO gram-molecules converted to alcohols is: $N_C = C_1OH + 2C_2OH + 3C_3OH + 4C_4OH + \ldots + nC_nOH$.

The selectivity $S_A$ is given by the formula:

$$S_A = 100 \times \frac{N_c}{(CO + CO_2) \text{g.mol}_{input} - (CO + CO_2) \text{g.mol}_{output}}$$

(The reaction by-products are methane, $C_2^+$ hydrocarbons and certain oxygenated compounds such as aldehydes, esters and ketones, present as traces).

The conditions of preliminary reduction of the catalysts are specified in Table 2 and reported in Tables 3 and 4.

Examples 1 to 18 illustrate the improved performance and stability of catalysts A to F.

Examples 2 and 4, respectively compared to Examples 3 and 5, show the favorable effect of the ($H_2$+CO+$CO_2$) partial pressure on the performance.

Examples 5 to 8 show the influence of the average $H_2$/CO (molar) ratio on the performance of catalyst B. Although the productivities to alcohols r and p slightly decrease when the $H_2$/CO ratio decreases, this decrease is accompanied with a substantial increase of the selectivity by weight to higher alcohols ($S_{C_2+OH}\%$) without noticeable decrease of the selectivity to alcohols, $S_A$, which remains very good.

Example 13 (compared with Example 12) shows that, at higher $CO_2$ concentration (8.9% instead of 1.3%) the activity and performance of catalyst D4 are slightly reduced ($S_{C_2+OH}$, $S_A$); simultaneously, the water proportion in the produced alcohols increases from 1.5% by weight to 10.8% by weight, thus requiring a further fractionation.

Example 17 (compared with Example 13) shows the promoter effect of palladium and rhodium additional metals on the activity (lower reaction temperature) and on the performance.

Examples 19 to 23 describe the results obtained with the comparison catalysts G, H, I and J. During the feed of synthesis gas, a substantial methanation reaction occurs in the presence of catalyst I; the temperature increase in the bed (T=250° C. before the synthesis gas supply) was about 150° C. (maximum temperature=400° C.), which explains the bad performance, after a relative stabilization of the temperatures.

TABLE 1

| Catalysts (formulas) | % b. w. of metal in proportion to the total weight of metals | | | | | | | Atomic ratios | | | Filling density |
| | Cu | Co | Zn | Zr | A | M | N | Cu/Co | $\frac{Zn + Zr}{Co}$ | $\frac{Zn}{Zn + Zr}$ | |
| --- | --- | --- | --- | --- | --- | --- | --- | --- | --- | --- | --- |
| A    $Cu_{0.8}Co_{0.6}Zr_{1.0}Zn_{0.5}Na_{0.046}K_{0.016}$ | 24 | 16.7 | 15.44 | 43.07 | 0.8 | 0 | 0 | 1.33 | 2.5 | 0.333 | 1.12 |
| $A_1$  $Cu_{0.7}Co_{0.5}Zn_{1.7}Zr_{0.05}Na_{0.012}$ | 23.40 | 15.30 | 58.50 | 2.40 | 0.15 | 0 | 0 | 1.4 | 3.5 | 0.97 | 1.15 |
| B    $Cu_{1.7}Co_{0.8}Zn_{1.0}Ce_{0.2}K_{0.045}Rb_{0.06}$ | 43.1 | 18.8 | 26.06 | 0 | 0.91 | 11.17 | 0 | 2.12 | 1.25 | 1 | 1.18 |
| C    $Cu_1Co_{0.4}Zr_{0.6}Zn_{1.4}Nd_{0.2}Na_{0.169}Cs_{0.0045}$ | 23.8 | 8.84 | 34.32 | 20.52 | 1.69 | 10.82 | 0 | 2.5 | 5 | 0.7 | 1.05 |
| D1   $Cu_{1.3}Co_{0.5}Zn_{1.2}Na_{0.012}$ | 43.3 | 15.44 | 41.12 | 0 | 0.15 | 0 | 0 | 2.6 | 2.4 | 1 | 1.35 |
| D2   $Cu_{1.3}Co_{0.5}Zn_{1.2}Na_{0.012}$ | 43.3 | 15.44 | 41.12 | 0 | 0.15 | 0 | 0 | 2.6 | 2.4 | 1 | 1.30 |
| D3   $Cu_{1.3}Co_{0.5}Zn_{1.2}Na_{0.012}$ | 43.3 | 15.44 | 41.12 | 0 | 0.15 | 0 | 0 | 2.6 | 2.4 | 1 | 1.30 |
| D4   $Cu_{1.3}Co_{0.5}Zn_{1.2}Na_{0.012}$ | 43.3 | 15.44 | 41.12 | 0 | 0.15 | 0 | 0 | 2.6 | 2.4 | 1 | 1.23 |
| E    $Cu_{0.9}Co_{0.45}Zr_{0.1}Zn_{1.1}La_{0.05}Pr_{0.07}K_{0.03}$ | 31.3 | 14.51 | 39.36 | 4.99 | 0.64 | 9.2 | 0 | 2 | 2.67 | 0.916 | 1.23 |
| F    $Cu_{1.3}Co_{0.5}Zn_{1.2}Na_{0.012}Pd_{0.09}Rh_{0.005}$ | 43.0 | 15.33 | 40.8 | 0 | 0.15 | 0 | 0.75 | 2.6 | 2.4 | 1 | 1.35 |
| G*   $Cu_1Co_{0.5}Zr_{1.5}K_{0.054}$ | 27.4 | 12.7 | 0 | 59.0 | 0.91 | 0 | 0 | 2 | 3 | 0 | 1.2 |
| H*   $Cu_1Co_{0.5}Zr_{1.5}Zn_{0.625}K_{0.054}$ | 23.29 | 10.80 | 14.98 | 50.15 | 0.77 | 0 | 0 | 2 | 4.25 | 0.04 | 1.17 |
| I*   $Cu_{0.8}Co_{0.84}Zn_{1.17}K_{0.11}$ | 28.07 | 27.33 | 42.33 | 0 | 2.37 | 0 | 0 | 0.95 | 1.39 | 1 | 1.04 |
| J*   $Cu_{1.01}Co_{0.025}Zn_{0.13}K_{0.027}Rb_{0.016}$ | 86.55 | 1.99 | 11.46 | 0 | 3.17 | 0 | 0 | 40.4 | 5.2 | 1 | 1.10 |

*Comparison catalysts

TABLE 2

Conditions of preliminary reduction of the catalysts
(Tests described in tables 3 and 4)

Reduction mode:

(a) 2% hydrogen in nitrogen atmospheric pressure
hourly volume velocity: 1 500 h$^{-1}$
24 h - stage at 160-190-210° C.
8 h - stage at 240° C.

(b) conditions (a) but with a total pressure of 0.5 MPa
1% H$_2$ in nitrogen and
hourly volume velocity of 1 000 h$^{-1}$ (c) conditions (a) but with
a total pressure of 0.5 MPa
1% H$_2$ in nitrogen
24 h stage at 160 and 190° C.
8 h stage at 210° C.
12 h stage at 240° C.

(d) conditions (c) with an additional 10 h - stage at 270° C.

(e) conditions (c) with two additional stages and a modification:
8 h stage at 240° C.
8 h stage at 270° C.
10 h stage at 300° C.

TABLE 3

| Ex | Cat | Red | Performances at t hours | VVH h$^{-1}$ | CO$_2$ vol. % | H$_2$/CO mol | P | T° C. | r | P | $S_{C_2+OH}$ % | $S_A$ % |
| --- | --- | --- | --- | --- | --- | --- | --- | --- | --- | --- | --- | --- |
| 1 | A | a | 145 | 3 000 | 0.8 | 1.7 | 6 | 290 | 0.11 | 0.12 | 44 | 77 |
| 2 | A | a | 500 | 3.000 | 0.8 | 1.7 | 10 | 290 | 0.16 | 0.179 | 41 | 78 |
| 3 | B | e | 145 | 10 000 | 1.1 | 2 | 6 | 280 | 0.11 | 0.13 | 46 | 75 |
| 4 | B | e | 800 | 10 000 | 1.1 | 2 | 10 | 290 | 0.195 | 0.23 | 43 | 76 |
| 5 | B | e | 900 | 3 000 | 1.0 | 2.2 | 8 | 290 | 0.13 | 0.153 | 40 | 76 |
| 6 | B | e | 1 050 | 3 000 | 0.9 | 1.5 | 8 | 290 | 0.115 | 0.136 | 45 | 75 |
| 7 | B | e | 1 120 | 3 000 | 0.8 | 1.0 | 8 | 290 | 0.10 | 0.118 | 56.8 | 69 |
| 8 | B | e | 1 210 | 3 000 | 1.0 | 2.2 | 8 | 290 | 0.125 | 0.148 | 41 | 77 |
| 9 | D1 | c | 145 | 6 000 | 1.3 | 1.6 | 6 | 290 | 0.06 | 0.081 | 42 | 74 |
| 10 | D2 | c | 145 | 6 000 | 1.3 | 1.6 | 6 | 290 | 0.09 | 0.117 | 36 | 78 |
| 11 | D3 | c | 145 | 6 000 | 1.3 | 1.6 | 6 | 290 | 0.105 | 0.136 | 38 | 80 |
| 12 | D4 | c | 145 | 6 000 | 1.3 | 1.6 | 6 | 290 | 0.095 | 0.117 | 40 | 75.5 |
| 13 | D4 | c | 300 | 6 000 | 8.9 | 1.6 | 6 | 290 | 0.080 | 0.098 | 38 | 73.8 |
| 14 | C | b | 145 | 4 000 | 1 | 1.5 | 8 | 295 | 0.120 | 0.126 | 46 | 76 |
| 15 | C | b | 145 | 10 000 | 1 | 1.5 | 18 | 400 | 1.10 | 1.21 | 50 | 68.5 |
| 16 | E | d | 145 | 8 000 | 0.8 | 1.5 | 6 | 290 | 0.10 | 0.123 | 39.2 | 79 |
| 17 | F | c | 145 | 6 000 | 1.3 | 1.6 | 6 | 280 | 0.105 | 0.142 | 44 | 76 |
| 18 | A1 | a | 145 | 3 000 | 0.8 | 1.7 | 8 | 290 | 0.12 | 0.14 | 42 | 79 |
| 19 | G* | b | 145 | 5 000 | 1.0 | 2 | 8 | 295 | 0.08 | 0.096 | 34 | 69 |
| 20 | H* | b | 145 | 6 000 | 1 | 2 | 8 | 300 | 0.09 | 0.105 | 36 | 67.5 |
| 21 | I* | e | 72 | 6 000 | 1.2 | 2 | 8 | 280 | 0.02 | 0.02 | 49 | 46 |
| 22 | J* | e | 145 | 10 000 | 1.1 | 2 | 6 | 280 | 0.03 | 0.04 | 14 | 75 |
| 23 | J* | e | 145 | 10 000 | 1.1 | 2 | 18 | 400 | 0.65 | 0.715 | 32 | 62 |

Ex = Example,
Cat = Catalyst,
red. = Reduction procedure,
P = (H$_2$ + CO + CO$_2$) partial pressure in MPa,
*comparison catalysts.

TABLE 4

| Ex | Cat | Red | VVH h$^{-1}$ | CO$_2$ vol % | H$_2$/CO mol | P | T° C. | r | p | S$_{C_2+OH}$ % | S$_A$% |
|---|---|---|---|---|---|---|---|---|---|---|---|
| 1 | A | a | 3 000 | 0.8 | 1.7 | 8 | 295 | 0.12 | 0.134 | 45 | 76 |
| 3 | B | e | 10 000 | 1.1 | 2 | 6 | 292 | 0.10 | 0.118 | 42 | 78 |
| 9 | D1 | c | 6 000 | 1.3 | 1.6 | 8 | 290 | 0.06 | 0.081 | 40 | 75.5 |
| 10 | D2 | c | 6 000 | 1.3 | 1.6 | 8 | 290 | 0.085 | 0.110 | 35 | 78.5 |
| 11 | D3 | c | 6 000 | 1.3 | 1.1 | 8 | 290 | 0.110 | 0.143 | 37 | 80 |
| 12 | D4 | c | 6 000 | 1.3 | 1.6 | 8 | 290 | 0.09 | 0.111 | 38 | 76 |
| 14 | C | b | 4 000 | 1 | 1.5 | 9 | 295 | 0.13 | 0.137 | 44 | 77 |
| 16 | E | d | 8 000 | 0.8 | 1.5 | 6 | 305 | 0.105 | 0.129 | 38 | 80 |
| 17 | F | c | 6 000 | 1.3 | 1.6 | 8 | 285 | 0.10 | 0.135 | 47 | 75 |
| 19 | G* | b | 4 000 | 1 | 2 | 10 | 305 | 0.07 | 0.084 | 31 | 58.5 |
| 20 | H* | b | 4 000 | 1 | 2 | 10 | 300 | 0.06 | 0.07 | 38 | 64 |

Ex = example,
Cat = Catalyst,
red = reduction procedure,
P = (H$_2$ + CO + CO$_2$) partial pressure in MPa
*Comparison catalysts.

What is claimed as the invention is:

1. A process for manufacturing saturated primary alcohols by reacting at least one carbon oxide with hydrogen in the presence of a catalyst consisting essentially of the following elements: copper, cobalt, zinc, at least one metal A selected from the group consisting of alkali metals and alkaline-earth metals, zirconium, at least one metal M selected from the group consisting of scandium, yttrium and rare-earth metals of atomic numbers from 57 to 71 inclusive or at least one metal N selected from the group consisting of noble metals from group VIII of the periodic classification of elements, wherein:

(a) the amount of each metal element, expressed in proportion to the total weight of the metals is:

| | |
|---|---|
| copper | 15–55% |
| cobalt | 5–25% |
| zinc | 15–70% |
| metal A | 0.01–5% |
| zirconium | 0–55% |
| metal M | 0–20% |
| metal N | 0–1% |

(b) The sum of the zinc and zirconium weights expressed in proportion to the total weight of the metals, is from 15 to 70%;

(c) The atomic ratios of these metals are:

| | |
|---|---|
| Cu/Co | = 0.2:1 to 5:1 |
| Zn/(Zn + Zr) | = 0.05:1 to 1:1 |
| (Zn + Zr)/Co | = 0.5:1 to 8:1. |

2. A process according to claim 1, wherein:
(a) The amount by weight of each metal element, in proportion to the total weight of the metals, is:

| | |
|---|---|
| copper | 15–55% |
| cobalt | 5–25% |
| zinc | 15–70% |
| zirconium | 1–45% |
| metal A | 0.01–5% |
| metal M | 0–20% |
| metal N | 0–1% |

(b) The sum of the zinc and zirconium weights, expressed in proportion to the total weight of the metals, is from 20 to 65%

(c) The atomic ratios of these metals are:

| | |
|---|---|
| Cu/Co = | 0.5:1 to 3.5:1 |
| Zn/(Zn + Zr) = | 0.1:1 to 0.98:1 |
| (Zn + Zr)/Co = | 1:1 to 5.5:1 |

3. A process according to claim 1, wherein the amount of metal M, expressed in proportion to the total weight of the metals, is from 0.1 to 15%.

4. A process according to claim 1, wherein the amount of metal N, expressed in proportion to the total weight of the metals, is from 0.01 to 0.8%.

5. A process according to claim 1, wherein the catalyst results from the drying and thermal activation of a hydrated precursor, which precursor is at least partly crystallized, and is obtained by coprecipitation of a first solution of soluble salts of copper, cobalt, and zinc of total concentration at most equal to 1 gram-atom of metals per liter and a second solution of a carbonate, bicarbonate or hydroxide of an alkali metal or ammonium, of total concentration at most equal to 2 gram-atoms of alkali metals or NH$_4$+ per liter the coprecipitation reaction being conducted at a pH of 7±1 pH unit, at a temperature of a least 50° C. and with a residence time in the reaction medium of at least 2 minutes the hydrated coprecipitate being then washed until its alkali metal content (weight of alkali metals expressed in proportion to all the metals) is reduced to a value from 0.01 to 0.4%.

6. A process according to claim 1, wherein the catalyst results from the drying and thermal activation of a hydrated precursor, whose structure, determined by X-ray diffraction, is amorphous, obtained by coprecipitation between a first solution of soluble salts of copper, cobalt, and zinc at a total concentration higher than or equal to 1 gram-atoms of metals per liter and a second solution of carbonate, bicarbonate or hydroxide of an alkali metal or ammonium, at a total concentration of at least 2 gram-atoms of alkali metals or ammonium per liter, the coprecipitation reaction being conducted at a pH of 7±1 pH unit, at a temperature ranging from 0° to about 30° C. and with a residence time in the reaction medium of at most 5 minutes, the hydrated precursor being then directly washed until its alkali metal content (expressed as the weight of alkali metals in proportion to all the metals) is reduced to a value from 0.05 to 5% by weight.

7. A process according to claim 5, wherein the alkali metals are introduced in the catalyst through said solution of carbonate, bicarbonate or hydroxide of said metals, the washing step being conducted so as to keep from 0.09 to 3.5% by weight of alkali metals, the washed precipitate being then dried, then thermally activated at 250°–600° C. for at least 0.5 hour.

8. A process according to claim 1, wherein the catalyst is subjected to a reduction before use, said catalyst reduction being performed by contact with a mixture of inert gas with at least one reducing compound in a molar ratio "reducing gas/inert gas+reducing gas" from 0.001:1 to 1:1, said reducing gas being hydrogen, carbon monoxide, an alcohol or a $C_1$–$C_2$ aldehydes, the reduction being conducted between 100° and 350° C., under a total pressure from 0.1 to 5 MPa, at an hourly volume velocity from 50 to 10,000 hours$^{-1}$ (NTP).

9. A process according to claim 1, wherein the reaction of carbon oxides with hydrogen is conducted at 250°–350° C., under a partial pressure of the hydrogen and carbon oxides (CO, $CO_2$) mixture from 2 to 15 MPa and with an average $H_2$/CO molar ratio in the reaction zone from 0.1:1 to 4:1 a VVH from 1 000 to 40 000 h$^{-1}$, the average $CO_2$ content in the reaction zone being from 0 to 5% by volume.

10. A process according to claim 1, wherein the reaction of carbon oxides with hydrogen is conducted in the presence of a liquid phase comprising one or more hydrocarbons having at least 5 carbon atoms per molecule.

11. A process according to claim 5, wherein the first solution further contains a soluble salt of zirconium, at least one metal M, at least one metal N, or a mixture thereof; the total concentration of metals per liter is 0.1 to 0.6 gram atoms per liter; and the second solution is a carbonate, bicarbonate or hydroxide of sodium, potassium, ammonium or a mixture thereof, with a concentration of 0.2 to 1.2 gram-atoms per liter.

12. A process according to claim 11, wherein at least one alkali or alkaline-earth metal is subsequently added to the hydrated precipitate by contact with the precipitate, then drying.

13. A process according to claim 11, wherein the coprecipitation reaction is conducted with a residence time in the reaction medium of at least 5 minutes, the hydrated coprecipitate being matured in the presence of its mother-liquors, and washed until its alkali metal content is reduced to a value of 0.05 to 0.2%.

14. A process according to claim 13, wherein subsequent to washing the hydrated coprecipitate is matured in the presence of its mother-liquors and liquid water, at about 15° C. to 250° C. for 15 minutes to 5 hours.

15. A process according to claim 6, wherein the first solution further contains a soluble salt of zirconium, at least one metal M, at least one metal N or a mixture thereof, and the second solution is a carbonate, bicarbonate or hydroxide of sodium, potassium, ammonium or a mixture thereof.

16. A process according to claim 12, wherein the precipitate, subsequent to contact with the alkali or alkaline earth metal is subjected to filtration, maturation, and spray-drying at 100°–250° C. for at least 10 seconds.

17. A process according to claim 8, wherein the reaction is conducted at a temperature of 130° to 320° C., a total pressure of 0.2 to 2 MPa, and VVH of 100 to 5,000 hours$^{-1}$ (NTP).

18. A process according to claim 9, wherein the reaction is conducted at a temperature of 260°–320° C., a partial pressure of hydrogen and carbon oxides of 5–12 MPa, an average $H_2$/CO molar ratio in the reaction zone of 0.2:1 to 3.5:1, a VVH of 2,000 to 20,000 hours$^{-1}$ and an average $CO_2$ content in the reaction zone of 0.1 to 3% by volume.

* * * * *